United States Patent [19]

Van Saun et al.

[11] Patent Number: 4,486,588

[45] Date of Patent: Dec. 4, 1984

[54] CYCLOHEXADIENE CARBOXYLATE INSECTICIDE INTERMEDIATES

[75] Inventors: William A. Van Saun, Titusville; David M. Roush, West Trenton, both of N.J.

[73] Assignee: FMC Corporation, Philadelphia, Pa.

[21] Appl. No.: 435,164

[22] Filed: Oct. 19, 1982

Related U.S. Application Data

[62] Division of Ser. No. 312,591, Oct. 19, 1981, abandoned.

[51] Int. Cl.³ .................................... C07C 295/14
[52] U.S. Cl. .................. 544/172; 544/58.1; 546/238; 546/239; 548/400
[58] Field of Search .............. 544/58.1, 172; 546/238, 546/239; 548/400

[56] References Cited

U.S. PATENT DOCUMENTS 3,201,397 8/1965 Brannock .................... 546/238

*Primary Examiner*—Robert W. Ramsuer
*Attorney, Agent, or Firm*—R. L. Hansen; H. R. Ertelt

[57] ABSTRACT

Precursors to benzyl compounds, useful in the manufacture of pyrethroid insecticides, are prepared by regiospecific addition of an enamine to a heterocyclic diene accompanied by elimination of volatile by-products.

4 Claims, No Drawings

CYCLOHEXADIENE CARBOXYLATE INSECTICIDE INTERMEDIATES

This application is a division of application Ser. No. 312,591, filed 10/19/81, abandoned.

This invention is in the field of chemical processes; more specifically, addition of an enamine to a heterocyclic diene, coupled with eliminations, which produces only one of two expected structural isomers and provides precursors to benzyl compounds useful in the manufacture of pyrethroid insecticides.

Pyrethroid insecticides, organic esters which contain acid moieties derived from cyclopropane and closely related carboxylic acids, coupled with various alcohols, are of great commercial interest throughout the world. A wide variety of alcohols appear in pyrethroid insecticides, e.g., substituted benzyl alcohols, such as those with methyl substituents. The insecticidal activity of 2,3,6-trimethylbenzyl chrysanthemate and related compounds is known [Elliott, et al., *Pestic. Sci.,* 1, 220 (1970)]. In fact, a number of appropriately substituted benzyl compounds, not only the benzyl alcohols, but also the corresponding benzyl chloride, bromides, tosylates, mesylates, and equivalents can be reacted with known pyrethroid acid compounds to produce insecticidal esters.

Many of the desired benzyl compounds are difficult to prepare in sufficient yield and purity to make the derived pyrethroid esters commercially attractive, even though the insecticidal efficacy of the esters is high. Therefore, a better process leading to the benzyl compounds of interest represents a distinct advance in the chemical process art.

The Diels-Alder reaction between a conjugated diene and an olefin, to produce a substituted cyclohexene by 1,4 addition has been known since 1928 and is represented by the following chemical equation:

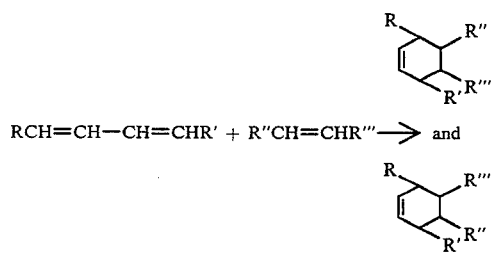

$$RCH=CH—CH=CHR' + R''CH=CHR''' \longrightarrow \text{and}$$

It will be readily apparent that two product structural isomers, as shown, are expected from such a reaction, because of the possibility of head-to-head and head-to-tail interaction between the diene and the olefin. In addition, for each structural isomer, eight racemic pairs are possible. Indeed, the stereochemistry of the Diels-Alder reaction has been the subject of a number of investigations, e.g., see *Chem. Rev.,* 61, 537 (1961). In view of the expected mixture, the Diels-Alder reaction is an unlikely candidate for a commercial process, where the absence of an intractable mixture of isomeric products with very similar properties must be avoided.

In spite of the improbability of avoiding an inseparable mixture of products in a Diels-Alder type reaction, it has now been found that precursors to the benzyl compounds desired in the manufacture of pyrethroid insecticides can be made cleanly. The new process turns out to be regiospecific, producing a single product isomer, eliminating problems associated with separating the product from a mixture of isomeric by-products. The process appears to involve addition of an enamine to a heterocyclic diene, akin to the Diels-Alder 1,4 cycloaddition illustrated above, but also benefits from unexpected and facile eliminations of carbonaceous and amine byproducts. The product carries an electron-withdrawing group readily converted to the benzyl function, e.g., by reduction. Thus, according to the process of this invention, a benzyl precursor of the formula

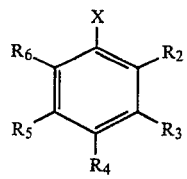

is prepared by reacting a heterocyclic diene of the formula

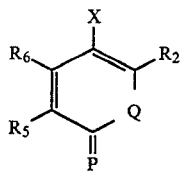

with an enamine of the formula

$$R_3HC=CR_4—NR_AR_B$$

under conditions such that the compounds CPQ and $R_A R_B NH$ are produced as by-products, and wherein X is an electron withdrawing group which can be converted to —$CH_2$—Y, wherein Y is hydroxyl or a leaving group readily displaced by carboxylate anions;

P and Q are independently oxygen or sulfur;

$R_A$ and $R_B$ are independently lower alkyl, or $R_A$ and $R_B$ are lower alkyl chains joined to form a ring, optionally with oxygen or sulfur in the ring;

$R_3$ and $R_4$ are independently hydrogen, lower alkyl, lower alkyl substituted with halogen, cycloalkyl, aryl, aryl substituted with halogen, lower alkyl, lower haloalkyl, lower alkoxy, lower haloalkoxy, or lower alkylthio, heteroaryl, heteroaryl substituted with halogen, lower alkyl, lower haloalkyl, lower alkoxy, lower haloalkoxy, or lower alkylthio; and $R_2$, $R_5$ and $R_6$ are independently selected from hydrogen, lower alkyl, lower haloalkyl, lower alkoxy, lower haloalkoxy, lower alkenyl, lower haloalkenyl, lower alkynyl, acyl, halogen, aryl, heteroaryl, aryl substituted with halogen, lower alkyl, lower haloalkyl, lower alkoxy, lower haloalkoxy, or lower alkylthio, thioaryl, acetyl, and methylaminocarbonyl.

Examples of substituent X include —CN, —$COR_8$, —$CON(R_8)_2$, —$COOR_9$, and —$COSR_9$, wherein $R_8$ is selected from hydrogen, lower alkyl, lower haloalkyl, and aryl; and $R_9$ is selected from aryl, lower alkyl, lower haloalkyl, and arylalkyl. Specific examples of X include methyl and ethyl carboxylates. Such substituents can be converted to —$CH_2$—Y, where Y is hydroxyl or a leaving group readily displaced by carboxylate anions, by methods known in the art. Such methods include reduction, e.g., with lithium aluminum hydride, as well as reaction with triphenyl phosphine and bromine, thionyl chloride or bromide, and methane sulfonyl chloride. Suitable leaving groups, Y, include, for example, halogen, especially bromine and chlorine; carboxylate, especially acetate; sulfonate, e.g.,

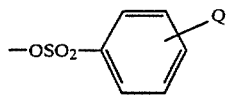

where Q is halogen, especially bromine, $C_1$–$C_6$ alkyl, e.g., p-toluene sulfonate, nitro, or hydrogen, and —O-$SO_2C_RH_SF_T$ where R is 1–4, e.g., methane sulfonate, and S and T are independently 0–9; and —$NR_3X$, where R may be $C_1$–$C_6$ alkyl, and X may be halogen, sulfonate, or other readily available anion.

In the case that P and Q are both oxygen, the heterocyclic diene is a pyrone. Where P and Q are both sulfur, the diene is a 2H-thiopyran-2-thione. The diene is a 2H-thiopyran-2-one or a 2H-pyran-2-thione in the cases that P is oxygen, Q is sulfur or P is sulfur, Q is oxygen, respectively.

$R_A$ and $R_B$, defined above, are specifically illustrated by methyl, ethyl, propyl, and isopropyl, for example. When $R_A$ and $R_B$ are both $C_2$ alkyl and they are joined by oxygen, the enamine is a morpholine derivative, when joined by sulfur, a thiamorpholine derivative. When $R_A$ and $R_B$ are lower alkyl chains joined without an oxygen or sulfur atom, e.g., to form a 6 or 5-membered ring, piperidine or pyrrolidine derivatives result, respectively.

Exemplary enamines include 4-(1-propenyl)morpholine, 4-(2-phenylethenyl)morpholine, methylethyl (2-phenylethenyl)amine, 4-(2-cyclohexylethenyl)morpholine, and 4-(2-isopropylethenyl)morpholine. Examples of heterocyclic dienes useful in this invention include 5-acetyl-3-chloro-6-methyl-2H-pyran-2-one, methyl 6-methyl-2-oxo-2H-pyran-5-carboxylate, phenylmethyl-2-oxo-2H-pyran-5-carboxylate, ethyl 4,6-dimethyl-2-oxo-2H-pyran-5-carboxylate, methyl 2-thio-2H-pyran-5-carboxylate, and methyl 6-phenyl-2-thio-2H-thiopyran-5-carboxylate.

Wherever used herein, the term "lower" modifying alkyl, haloalkyl, alkenyl, alkynyl, alkoxy, and so forth, means a straight or branched chain of 1–6 carbon atoms, preferably 1–4 carbon atoms; "cycloalkyl" means a ring containing 3–8 carbon atoms; and "halo", "halide", or "halogen" means fluorine, chlorine, or bromine, unless specifically stated otherwise.

The enamine starting materials are prepared by several methods known in the art. For example, enamines may be prepared by the reaction of a secondary amine with an aldehyde or a ketone. Enamines are also prepared by heating a secondary amine with a ketal, or from imines. A number of different methods for preparing enamines are described in A. G. Cook, Editor, "Enamines: Synthesis, Structure, and Reactions," Marcel Dekker, New York, N.Y., 1969, Chapter 2, and by S. F. Dyke in "The Chemistry of Enamines," Cambridge University Press, Cambridge, England, 1973, Chapter 1.

The heterocyclic dienes, which are the other starting material in the process, may be prepared by methods known in the art. Representative syntheses of pyrones are described by Ghosal in *Indian Journal of Chemistry*, 16B, 200 (1978), for example, and a number of them are available in commerce. Preparation of the sulfur-containing heterocyclic dienes is described in "Advances in Heterocyclic Chemistry," Vol. 8, Academic Press, New York, N.Y., pp. 219–241.

The process of this invention can be carried out either with or without a solvent. Suitable solvents include aromatic hydrocarbons, such as dichlorobenzene, toluene and xylene. When a solvent is employed, the reaction is generally carried out at reflux. The reaction may be completed more quickly in the absence of a solvent by employing higher temperatures.

A cyclohexene adduct from initial reaction of the enamine with the heterocyclic diene, believed to be produced, is not generally isolated, since CPQ, e.g., $CO_2$, is eliminated immediately, generating a cyclohexadiene. The latter may be isolated, as in Examples 3 and 4 below. These cyclohexadienes of the formula

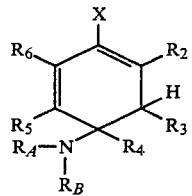

wherein X, $R_A$, $R_B$, and $R_2$–$R_6$ are as defined above, are intermediate compounds within the scope of this invention. Especially useful compounds of this formula are those wherein $R_A$ and $R_B$ are both $C_2$ alkyl and they are joined by oxygen to form a morpholine ring; those wherein X is lower alkyl carboxylate; and those wherein $R_2$ and $R_6$ are methyl, $R_4$ and $R_5$ are hydrogen, and $R_3$ is selected from phenyl, methyl, 1-methylethyl, and cyclohexyl. Generally speaking, however, it is preferable to conduct the reaction at a temperature sufficiently high so that by-product $R_AR_BNH$ is also eliminated during the process and can be removed, e.g., by distillation.

It is possible to begin with preparation of the enamine, and then, without isolating it, react it with the heterocyclic diene as illustrated in Example 2 below.

The process of this invention is described in greater detail and more specifically by reference to the following Examples. In the Examples, unless otherwise indicated, all temperatures are in degree Celsius and pressures are in millimeters of mercury. Proton chemical shifts, taken from nmr spectra in $CDCl_3$, are reported in ppm with respect to tetramethylsilane.

EXAMPLE 1

Ethyl 2,4-Dimethyl-[1,1'-biphenyl]-3-carboxylate (a) Under a dry nitrogen atmosphere a solution of commercial ethyl 4,6-dimethyl-2-oxo-2H-pyran-5-carboxylate (19.6 g, 0.1 mole) in toluene (20 ml) was added dropwise to a stirred solution of 4-(2-phenylethenyl)-morpholine (14.3 g, 0.076 mole) in toluene (200 ml). Preparation of the morpholine derivative is described in U.S. Pat. No. 3,922,237. After the addition, the reaction mixture was heated at reflux for approximately 20 hours. The reaction mixture was then cooled and concentrated under reduced pressure, leaving a residue. The residue was heated at 170° under a dry nitrogen atmosphere for 3.5 hours, allowed to cool to room temperature, and then filtered. The filtrate was purified by column chromatography on silica gel, elution first with n-hexane: ethyl acetate, and finally ethyl acetate, to give ethyl 2,4-dimethyl-[1,1'-biphenyl]-3-carboxylate (3.5 g) as a yellow oil.

Analysis: nmr (δ): 1.37(t,3H); 2.20(s,3H); 2.33(s,3H); 4.37(q,2H); 6.87-7.47(bm,7H).

(b) A stirred solution of phenylacetaldehyde (77.0 g, 0.64 mole) and morpholine (56.0 g, 0.64 mole) in toluene (500 ml) was heated at reflux until the theoretical amount of water was collected in a Dean-Stark trap. The reaction mixture was cooled slightly, and ethyl 4,6-dimethyl-2-oxo-2H-pyran-5-carboxylate (125.0 g, 0.64 mole) was added. The solvent was distilled from the reaction mixture at atmospheric pressure to leave a residue. The residue was then heated at 200° for 2.5 hours. A Dean-Stark trap was used to collect the distilled morpholine. The remaining pot residue was cooled and slurried with a mixture of silica gel (700 g) and methylene chloride (1500 ml) for 45 minutes. The slurry was filtered and the filter cake rinsed with methylene chloride (500 ml). The combined filtrates were evaporated under reduced pressure to leave a thick brown residue. This residue was distilled under reduced pressure to give several fractions. All fractions which contained more than 73% product by gc analysis were combined to give a total of 90.5 g crude ethyl 2,4-dimethyl-[1,1'-biphenyl]-3-carboxylate.

The ester is reduced, e.g., with lithium aluminum hydride, to produce (2,4-dimethyl-[1,1'-biphenyl])-3-methanol.

EXAMPLE 2

Ethyl 2,6-Dimethyl-3-(1-methylethyl)benzoate

Morpholine (13.34 g), isovaleraldehyde (13.18 g), p-toluene sulfonic acid (0.2 g), and toluene (300 ml) were combined and heated at reflux using a Soxhlet extractor containing magnesium sulfate to remove any water produced. After three hours the Soxhlet extractor was replaced with a condenser, and ethyl 4,6-dimethyl-2-oxo-2H-pyran-5-carboxylate (30 g) was added. The reaction mixture was heated under reflux for approximately 64 hours. The solvent was evaporated, and the resultant oil was distilled at atmospheric pressure to give 11.1 g of crude product which was chromatographed to yield ethyl 2,6-dimethyl-3-(1-methylethyl)benzoate (2.8 g).

Analysis: nmr (δ): 1.22(d,6H); 1.40(t,3H); 2.27(x,6H); 3.17(q,1H); 4.42(q,2H); 6.77-7.23(bm,2H).

[2,6-Dimethyl-3-(1-methylethyl)phenyl]methanol was prepared by reducing the ester with lithium aluminum hydride.

Other 2,6-dimethylbenzoates and corresponding methanols, those wherein the 3-substituent is lower alkyl other than 1-methylethyl, e.g., methyl, ethyl, n-propyl, butyl, pentyl, hexyl, iso-butyl, sec-butyl, etc., are similarly prepared by the method described above, substituting an aldehyde of appropriate structure for the isovaleraldehyde. For example, propanal gives rise to (2,3,6-trimethylphenyl)methanol, butyraldehyde to (2,6-dimethyl-3-ethylphenyl)methanol, 4-methylpentanal to (2,6-dimethyl-3-iso-butylphenyl)methanol, 3-methylpentanal to (2,6-dimethyl-3-sec-butylphenyl)methanol, and so forth. The enamine can, of course, be isolated if desired.

EXAMPLE 3

Ethyl 2,3,6-Trimethylbenzoate

A stirred solution of 4-(1-propenyl)morpholine (0.053 mole), prepared by the method of A. Tanara, et al., *Agr. Biol. Chem.* 37, 2365 (1973), and ethyl 4,6-dimethyl-2-oxo-2H-pyran-5-carboxylate (11.8 g, 0.06 mole) in 75 ml of toluene was heated at reflux for four hours. The reaction mixture was allowed to cool to room temperature and diluted with 75 ml diethyl ether. The mixture was washed with 10% aqueous hydrochloride acid (2×150 ml). The washes were combined and treated with aqueous sodium hydroxide until basic, then extracted with diethyl ether (2×150 ml). The extracts were combined, dried over anhydrous magnesium sulfate, and filtered. The filtrate was evaporated under reduced pressure to give 9.8 grams ethyl 4-(4-morpholino)-2,3,6-trimethyl-1,5-cyclohexadiene-1-carboxylate as an oil.

Analysis: nmr (δ): 1.00(d,3H); 1.33(t,3H); 1.88(d,3H); 1.91(s,3H); 2.05-2.77(m,5H); 2.88(d,1H); 3.68(t,4H); 4.28(q,2H); 5.40(d,1H).

Ethyl 4-(4-morpholino)-2,3,6-trimethyl-1,5-cyclohexadiene-1-carboxylate (9.7 g, 0.035 mole) was stirred and heated at 220° for three hours. A Dean Stark trap was used to collect the distilled morpholine. The reaction mixture was cooled to room temperature, diluted with 150 ml diethyl ether, and washed with aqueous hydrochloric acid (2×100 ml) and water (100 ml). The organic phase was dried over anhydrous magnesium sulfate and filtered. The filtrate was evaporated to yield 5.0 grams ethyl 2,3,6-trimethylbenzoate as an oil.

EXAMPLE 4

Ethyl 3-Cyclohexyl-2,6-dimethylbenzoate

In a manner similar to Example 3, the reaction of 4-(2-cyclohexylethenyl)morpholine (16.5 g), which was prepared by the method of Tanara, et al. cited above, with ethyl 4,6-dimethyl-2-oxo-2H-pyran-5-carboxylate (9.8 g, 0.05 mole) in toluene (75 ml) produced ethyl 3-cyclohexyl-2,6-dimethyl-4-(4-morpholine)-1,5-cyclohexadiene-1-carboxylate.

In a manner similar to Example 3, heating ethyl 3-cyclohexyl-2,6-dimethyl-4-(4-morpholino)-1,5-cyclohexadiene-1-carboxylate (10.6 g) at 255° produced an oil (2.7 g). This oil was combined with 0.9 g of an oil previously prepared in the same manner, and the total was distilled under reduced pressure to yield ethyl 3-cyclohexyl-2,6-dimethylbenzoate as an oil (1.9 g, b.p. 105°-115° C./0.1 mm).

Analysis: nmr (δ): 0.8-2.0(bm,11H); 1.38(t,3H); 2.30(s,6H); 4.41(q,2H); 7.00(d,1H); 7.20(d,1H).

What is claimed is:

1. A chemical compound of the formula

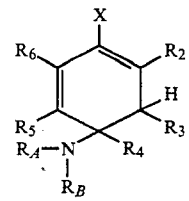

wherein

X is lower alkyl carboxylate;

$R_A$ and $R_B$ are lower alkyl chains joined to form a ring, optionally with oxygen or sulfur in the ring;

$R_3$ and $R_4$ may be hydrogen, lower alkyl, cycloalkyl, or aryl; and $R_2$, $R_5$, and $R_6$ are independently selected from hydrogen or lower alkyl.

2. A compound of claim 1 wherein $R_2$ and $R_6$ are methyl, $R_4$ and $R_5$ are hydrogen, $R_A$ and $R_B$ are $C_2H_4$ groups joined by oxygen to form a morpholine ring, and $R_3$ is selected from phenyl, methyl, 1-methylethyl, and cyclohexyl.

3. Ethyl 4-(4-morpholino)-2,3,6-trimethyl-1,5-cyclohexadiene-1-carboxylate.

4. Ethyl 3-cyclohexyl-2,6-dimethyl-4-(4-morpholine)-1,5-cyclohexadiene-1-carboxylate.

* * * * *